United States Patent [19]
Baumoel

[11] Patent Number: 6,062,091
[45] Date of Patent: May 16, 2000

[54] METHOD AND APPARATUS FOR DETERMINING ULTRASONIC PULSE ARRIVAL IN FLUID USING PHASE CORRELATION

[76] Inventor: Joseph Baumoel, 155 Plant Ave., Hauppauge, N.Y. 11788

[21] Appl. No.: 08/837,800

[22] Filed: Apr. 22, 1997

[51] Int. Cl.$^7$ .................................................... G01F 1/66
[52] U.S. Cl. ............................................................. 73/861.27
[58] Field of Search ................................ 73/861.28, 194, 73/861.27

[56] References Cited

U.S. PATENT DOCUMENTS

| | | | |
|---|---|---|---|
| 3,987,674 | 10/1976 | Baumoel | 73/194 A |
| 4,520,320 | 5/1985 | Potzick et al. | 328/133 |
| 5,163,663 | 11/1992 | Gill | 73/861.28 |
| 5,178,018 | 1/1993 | Gill | 73/861.28 |

*Primary Examiner*—Harshad Patel
*Assistant Examiner*—Jewel V. Thompson
*Attorney, Agent, or Firm*—Ostrolenk, Faber, Gerb & Soffen, LLP

[57] ABSTRACT

Apparatus for determining the arrival time of a sonic signal transmitted through a fluid medium flowing in a vessel comprising, a transmitter for generating a sonic signal for transmission through the fluid in the fluid carrying vessel, the sonic signal having at least one marker embedded therein, a receiver for receiving the marked sonic signal after transmission of the signal in the fluid, and a detector for sensing the marker in the marked sonic signal at the receiver, the transmitter and receiver each comprising a wide beam ultrasonic transducer.

28 Claims, 7 Drawing Sheets

$$V_F = \frac{K_C \Delta T}{T_L}$$

$$T_N = T_L T_{DEL}$$

$\ell pd\ell = \ell pu\ell$
$\ell puh \gg \ell pdh$

METHOD AND APPARATUS FOR DETERMINING ULTRASONIC PULSE ARRIVAL IN FLUID USING PHASE CORRELATION

BACKGROUND OF THE INVENTION

The present invention relates to ultrasonic flow metering. Ultrasonic flow metering, or the determination, using ultrasonic energy, of flow velocity through a conduit, such as a pipeline, is based on determining the effect of fluid flow on the upstream versus downstream transmission time of an ultrasonic signal passing diagonally through the fluid in the pipeline. Ultrasonic flow metering is particularly advantageous because it can be performed non-intrusively, i.e., without requiring intrusion into the pipeline. The ultrasonic flow meter transmitting and receiving transducers are suitably clamped on to the pipeline and ultrasonic signals are injected through the pipewall. The flow rate is determined by measuring the difference in transit time between upstream and downstream ultrasonic signals. Since the effect of flow on transit-time, even at high flow velocities, is small, it is essential to avoid even small uncertainties in this measurement. Unfortunately, the ultrasonic signal which is used for detection is of low resolution relative to the needed time detection resolution, since it generally consists of waves of periods of from hundreds to thousands of nanoseconds, while the needed detection resolution is of the order of from picoseconds to only a few nanoseconds at best.

In addition, to detect the arrival time of the sonic signal implies that there is a detectable "beginning" of the signal. Unfortunately, the signal does not arrive with a sharp front edge, but rather is a relatively slow buildup of a basically sinusoidal waveshape, due to the high "Q" of the ultrasonic transmitter, as well as the sonic resonance of the pipe wall or other structure through which the wave must pass in order to enter the liquid stream. These metallic structures are generally highly resonant, and contribute to the slow buildup of the waveshape. Thus at best, the beginning of the signal is hard to detect, and an error in detecting the arrival by even only one cycle of the receive signal frequency has a disastrous effect on the measured flow due to this effect on the apparent upstream versus downstream detection time difference.

Furthermore, even if the first arrival cycle is robust, it must be recognized that there is a background level of noise, much of it at the frequency of the receive signal itself, and therefore unfilterable. Accordingly, in present systems, detection of the actual arrival time of the beginning of the receive signal is either very difficult, uncertain as to its arrival time, or simply impossible in any real way, depending on the actual character of the signal and the ambient noise present when it arrives.

SUMMARY OF THE INVENTION

The present invention provides a method and apparatus for accurate determination of the arrival time of an ultrasonic signal transmitted through a fluid medium in a pipeline. More particularly, the invention allows accurate flow determination by assuring that the signals received after transmission in both upstream and downstream directions through the flowing fluid of a pipeline at the receiving transducer are in the same relative relationship. Even more particularly, the invention assures that detection windows for both upstream and downstream signals are in the same absolute and relative relationship to the received signals, and in particular, to upstream and downstream signal phase markers embedded in the transmitted signals. This allows accurate transit time determination by phase detection, and thus accurate flow measurement.

The invention thus provides correlation of the flow detection time windows for the upstream and downstream received signals based on the detection of a transmitted marker in the received signals.

Accordingly, the invention provides for accurate determination of the arrival time of the transmitted marker to enable correlation of the received signals for accurate transit time determination, particularly by phase detection, and thus accurate flow measurement.

Flow (VF), as known to those of skill in the art, is equal to a dimensioned constant, Kc (vol/time), multiplied by the ratio of delta t ($\Delta$t), the upstream minus downstream transit-time difference, and TL, the average transit time through the liquid. Accordingly, VF=Kc ($\Delta$t)/TL.

The primary reason for needing to identify the relative arrival time of the received signal is that a misregistration of the arrival time as represented by either UP and DN signals (to be described later) would cause a measured time difference between upstream and downstream signals equal to the number of cycles of signal which was misregistered, and thus an error in the transit time difference $\Delta$t. Since each period of transmit signal is equivalent to a large $\Delta$t, a large error in measured flow rate would result. This error in $\Delta$t is referred to herein as misregistration.

In addition, as noted below, an absolute error in detection of arrival time of both upstream and downstream signals, even in the absence of a relative arrival time error, would still cause a flow measurement error, since this would affect the determination of the travel time TL of the signal in the liquid itself. This time appears in the denominator of the flow detection equation, above, and thus produces a proportional error in measured flow rate. This error in TL is referred to herein as misacquisition.

Accordingly, an object of this invention is to produce a measurement of upstream and downstream travel time which is accurate both in the relative and absolute sense.

Unfortunately, as previously noted, the actual arrival time of the leading edge of the signal is masked by background noise, which is occasionally even larger than the small magnitude of the leading edge of the signal itself. There is thus no direct means of measuring TN, which is the sum of TL and other known time delays $T_{DEL}$ in the arrival of the signal from transmission to reception. Therefore, according to the invention, it is necessary to mark the transmit signal, at a point a known time following the beginning of transmission, with at least one marker that can be detected in the receive signal. Thus, if the arrival time of the marker is determined, and it is known that it corresponds to a point in the transmit signal a known time after the beginning of transmission, it will be possible to compute the actual TN time and thus TL.

It must be recognized that the marker, as is the entire transmit signal, passes through a filter, effectively comprising the passband characteristics of the transducer, as well as the filter properties of the sonically resonant pipe wall itself. In addition, the Q of these factors is usually quite high, so that introducing a marker does not guarantee that it will be easily detected in the receive signal. Therefore, it is essential that the marker be robust, and substantially unaffected by changes in flow rate or in the sonic properties of the liquid itself.

It must also be recognized that, as liquid conditions change, the shape of the receive signal and the detectable properties of the marker can change. If the marker is not detected for each transmit-receive event, it is possible that a misregistration (detection of the upstream marker one or more cycles of receive signal different from the downstream detection) could occur. Therefore, it is essential that the marker placed in the transmit signal be effective in assuring against misregistration even under difficult signal conditions. In addition, it is essential also to assure that for both upstream and downstream signals, the absolute value of TN be properly determined. This is necessary to assure against the errors which would result in TN and TL which, from the flow equation above, would cause an error in measured flow rate equal to the percentage that the time error is relative to TL itself (misacquisition).

In ultrasonic flow meters manufactured by Controlotron Corp. of Hauppauge, N.Y., flow is detected by squaring the basically sinusoidal receive signal to create a square wave, and then determining the phase of this square wave with respect to a reference square wave whose phase and timing are known. The phase difference between the received signal and the reference is proportional to time delay or transit time. The reference square wave is a synthesized square wave of the same frequency as the received waveform, synchronous to the time at which the transmit signal was sent. One of the chief advantages of this system is that the received square wave is defined by zero crossovers of the received analog signal, and therefore immune to corruption of the amplitude of the signals, as may be possible in other forms of correlation detection. The two square wave signals (received and reference) are phase detected, and the relative timing is computed by use of an up/down counter, driven by the phase difference, counting a very high frequency asynchronous clock pulse output.

According to the invention, since flow detection in Controlotron flow meters is based on phase detection, a phase marker is embedded into the transmit signal by introducing a phase advance or delay at a selected point in the transmit burst, after achieving a steady state or constant phase condition, typically after a known number of cycles after the beginning of the burst. Thereafter inspecting the receive signal phase pattern for the first evidence of a change of phase in the receive signal will locate the corresponding cycle of the receive signal and provide a reference for opening of a time window during which phase detection is performed for determining transit time. This is performed for both upstream and downstream received signals. The time windows for both upstream and downstream received signals are correlated, i.e. placed in the same relationship to the marker, enabling determination of relative upstream/downstream transit time difference free of misregistration error. The times of arrival of the markers are used to determine absolute transit time TL free of misacquisition error.

The phase relationship between the receive signal and the reference square wave is detected by demodulating the receive signal against the reference digitally, counting the number of pulses of a high frequency asynchronous clock relative to the number of pulses developed by a full cycle of the receive frequency. If the counts are balanced, equal "Up and Down" (UP and DN) then the phase is, say, 90 degrees. If they are all UP, then the phase is 0. If all DN, then the phase is 180 degrees. Since the frequency of the count clock is high relative to the receive signal, and the counts are averaged for many cycles, the resolution of phase shift is exceedingly high, resulting in the ability to distinguish very small differences of phase shift.

The demodulation process starts by opening a flow phase detection window at a known time after the beginning of transmission when the signal transmitted through the liquid is expected to arrive, and then assuring that the time of arrival of the marker is a predefined number of cycles after the flow phase detection window opens. This is done by adjusting the time of opening of the window. The adjustment is made for both upstream and downstream signals. This ensures that the time windows for both upstream and downstream receive signals in which phase detection is made are correlated, or in registration. Based on the measured phases of the received signals during the correlated flow phase detection time windows for upstream and downstream signals, the upstream and downstream transit times are determined, and hence the transit time difference $\Delta t$. If either window is displaced a different number of cycles from its marker, this condition is defined as misregistration and results in a flow determination error. If both windows are displaced by the same number of cycles from the predefined number of cycles expected, this is defined as misacquisition and results in a flow determination error. The correlation technique according to the invention defeats both these errors.

According to the invention, a phase marker is embedded in each transmission cycle, and is detected as a sudden change in the phase of the cycles of receive signal following those cycles in which it is embedded. Since noise can affect this detection, it is generally necessary to digitally process a number of successive receive signals to extract this signal from the noise. In this way, sufficient data stability can be obtained to qualify that there is no misregistration which has affected the flow data which has been collected and processed simultaneously with collection and processing of the correlation data itself. In general, except for exceedingly noisy signal conditions, the time needed to qualify flow data is short, usually as short as, or almost as short as, the time needed for reasonable flow data collection, e.g., from 10 to 100 cycles of sonic transmission.

In larger pipes, and at higher flow rates, the location on the pipe wall at which the sonic energy will be received at the receive transducer can be significantly different from the location at which the beam emerges at lower flow rates. This is due to "beam blowing". The effect of flow (VF) is to move the apparent emergence point closer to the downstream transmit transducer and further from the upstream transmit transducer. Thus, there results a different distance of pipe travel between the upstream and downstream transmission directions. For smaller pipes and lower flow rates, the effect is less noticeable.

Applicant has previously discovered the existence of a sonic waveguide property in all pipes, in which a sonic wave will propagate with essentially equal phase and group velocities if the injected signal is at the resonant frequency of the pipe wall, and the phase velocity of the injected sonic signal matches the transverse mode sonic velocity as it travels axially down the pipe wall. Thus, dependent on the liquid refraction angle, the beams actually emerge some distance away from the transmit transducer. See U.S. Pat. Nos. 3,987,674 and 4,475,054. The resonant frequency is determined by the wall thickness and the longitudinal wave velocity of the pipe material. The phase velocity is determined by the pipe material, and to some extent is affected by the wall thickness, since the actual velocity is somewhat different from that of the bulk material.

If the transducer's sonic signal has a transmit frequency which matches a pipe's resonant frequency, and its injection angle matches the phase velocity of the transducer housing to the transverse mode phase velocity in the pipe wall material, then the shape and phase characteristics of the sonic wave in the pipe wall remains essentially constant as the wave travels axially down the pipe wall. Thus, even though, due to beam blowing, the amount of pipe travel may be different in the upstream and downstream directions, the resultant signal shape and phase characteristics will be essentially identical. Therefore, even though the sonic beam may be blown by high flow rates, the marker phase characteristics will remain identical, or at least sufficiently so for successful window position correlation.

Since such a transducer is the only type that can avoid beam blowing effects, it necessarily follows that only the so-called Controlotron wide beam transducer (U.S. Pat. No. 3,987,674), which matches the frequency and phase velocity waveguide characteristics of a particular pipe, can permit successful window position correlation independent of the effects of high flow velocity beam blowing. Therefore, all transducers which operate at a fixed single frequency, or a group of frequencies, none of which match the pipe's resonant frequency, and whose phase characteristic is not specifically matched to the material of a given pipe, cannot avoid a change in its amplitude shape and phase characteristic due to beam blowing, which causes the upstream and downstream signals to be different in this regard. Such a condition can cause both misregistration and misacquisition by preventing proper correlation.

Other features and advantages of the present invention will become apparent from the following description of the invention which refers to the accompanying drawings.

BRIEF DESCRIPTION OF THE DRAWINGS

The invention will now be described in greater detail in the following detailed description, with reference to the drawings, in which.

DETAILED DESCRIPTION OF EMBODIMENTS OF THE INVENTION

Figure 1:
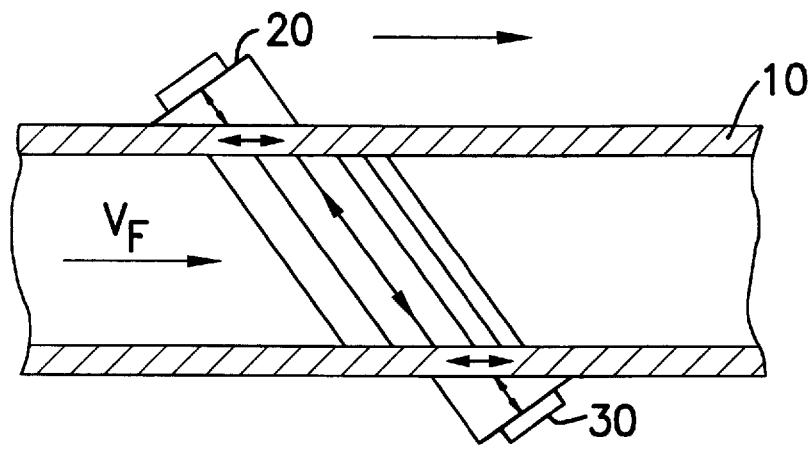
FIG. 1 shows a pair of ultrasonic transducers attached to a pipeline, shown in cross-section and used in an ultrasonic flow measurement system.

With reference now to the drawings, FIG. 1 shows a typical application of wide beam ultrasonic transducers used in an ultrasonic flow measurement system. The ultrasonic transducers are nonintrusive but may also be of the "wetted" or intrusive type, although beam blowing has a different effect for wetted transducers. Preferably, the transducers are of the clamp-on variety. They may be attached to opposite sides of the wall of a pipeline 10 whose flow is to be measured. The flow is indicated by the velocity vector VF in FIG. 1. As known to those of skill in the art, the transducers may also be located on the same side of the pipe, in which case reliance is made on the reflection from the opposite side pipewall.

As known to those of skill in the art, transmission of ultrasonic signals is made in both upstream and downstream directions. Accordingly, in a first instance, for example, ultrasonic transducer 20 may transmit a signal to ultrasonic transducer 30 to be used in the determination of the downstream transit time. Ultrasonic transducer 30 will then transmit an ultrasonic signal to transducer 20 to be used in the determination of the upstream transit time. As known to those of skill in the art, the fundamental means of flow detection by such clamp-on non-intrusive ultrasonic flow meters is the determination of the effect of the flow in the fluid in the pipeline on the upstream versus downstream transit time of a sonic beam injected and received by transducers on the pipe wall, as the beam passes through the flowing liquid. The transit time is shortened in the downstream direction and lengthened in the upstream direction in proportion to the velocity of the stream itself. By solving the equation of such a system, as known to those of skill in the art, it can be determined that VF=Kc Δt/TL where VF equals flow velocity; Kc equals a dimensioned calibration factor in units of vol/time; Δt equals the measured upstream minus downstream transit time difference and TL equals the measured average upstream and downstream transit time.

As shown in FIG. 1, TL is only part of the overall transit time TN between transducers. The overall transit time TN will include the transit time in the fluid TL plus known transit times through the transducer mounting blocks, pipeline walls, etc., indicated in FIG. 1 collectively as $T_{DEL}$.

Figure 8:
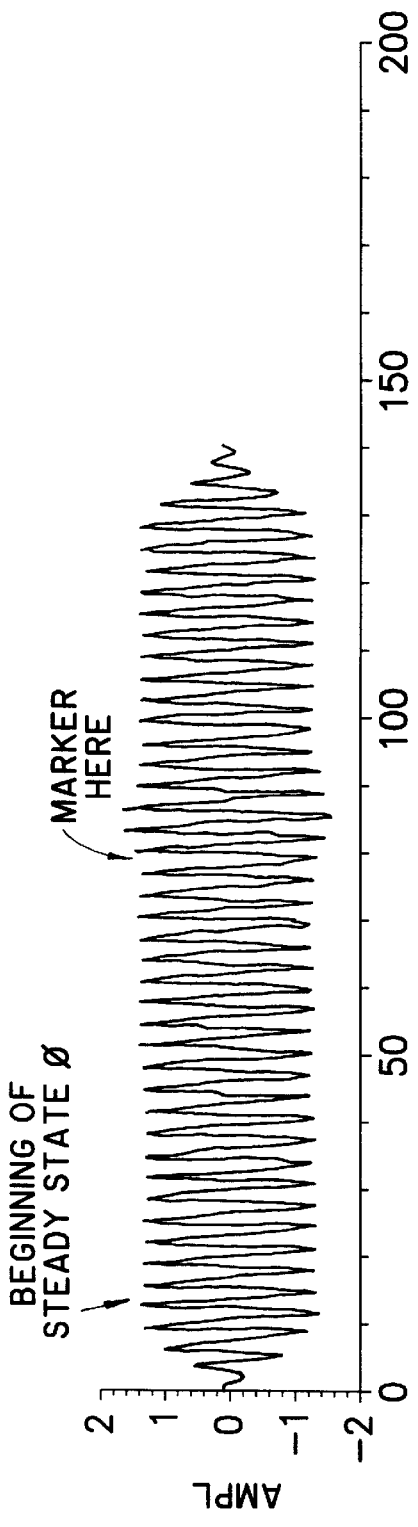
FIG. 8 is an amplitude plot of an illustrative receive signal.
Figure 7:
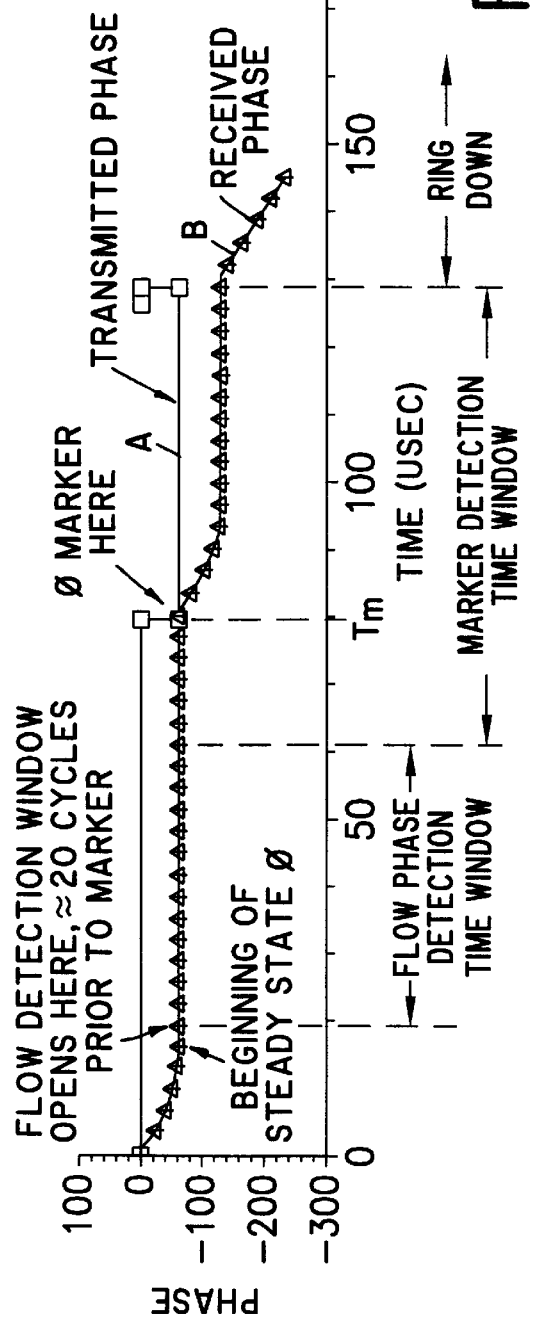
FIG. 7 is a phase plot of illustrative transmitted and received signals.

FIG. 7 shows the phase of an illustrative transmit signal (A) as transmitted by a transducer, for example, transducer 20 or 30, as well as the illustrative receive signal phase (B) received by the opposite or receiving transducer 30, 20 (depending upon whether the upstream or downstream transit time is being determined). According to the invention, a phase marker representing one or more abrupt changes in phase is added to the transmit signal. The phase marker is added at a time TM after transmission begins, ideally, a known number of cycles of transmit frequency. Because of effects of transmission through the liquid and pipe walls, etc. the receive signal is degraded and becomes essentially sinusoidal in shape, as shown in FIG. 8. However, according to the invention, despite the degradation of the received signal, the phase marker, because of the sudden change of phase, can be detected. This allows precise registration or correlation of the location of the timing windows for both upstream and downstream received signals, as will be explained below.

Figure 6:
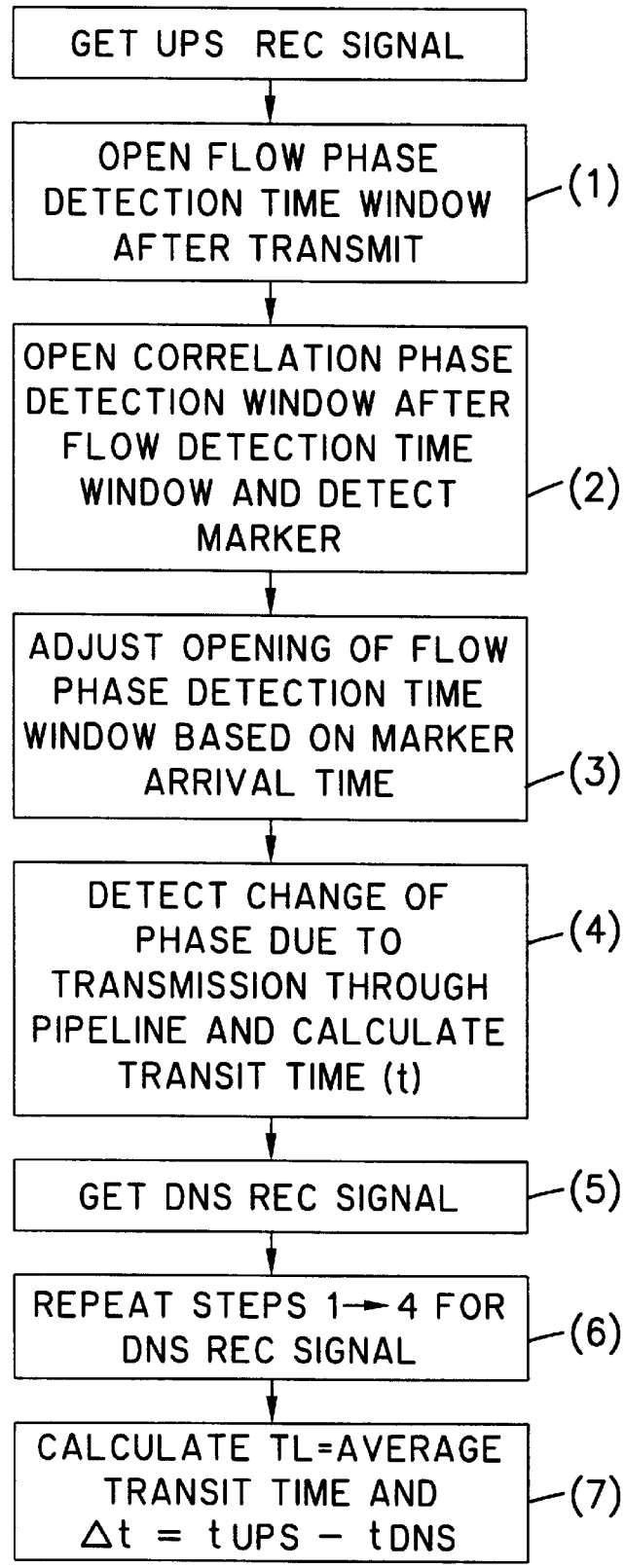
FIG. 6 is a flow-chart of the method for determining the arrival time of the receive signal as determined by the detection of the change of phase marker and showing how the transit time difference Δt between upstream and downstream signals as well as how the average transit time TL is determined.

FIG. 6 is a flowchart of a computer program showing how flow measurement is performed and particularly, the correlation of timing windows. The time difference Δt as well as the average transit time TL through the liquid, is determined first by opening a flow phase detection time window a predefined number of cycles after the beginning of transmission when the signal transmitted through the liquid is expected to arrive at the receiver (1). A second window called a correlation phase detection window is opened after the flow phase detection window during which the change of phase marker is detected (2). A phase detection circuit is used to detect the change of phase. The time at which the flow phase detection time window opens is then adjusted based on the time of arrival of the marker so that it is a predefined number of cycles before the marker (3). The phase detection circuit is utilized to detect the change of phase in the received signal due to transmission through the pipeline and the transit time is determined (4). This is done for both upstream and downstream (5), (6) receive signals so that the flow phase detection windows are in precise registration. The registration of the upstream and downstream signal windows allows accurate determination of Δt as the difference between the upstream and downstream transit times (7) as measured by the phase difference with respect to a reference signal. This technique of precisely aligning the flow phase detection windows for upstream and downstream receive signals is called, according to the invention, phase correlation. TL is determined based on the arrival time of the markers with respect to the beginning of transmission (7).

FIGS. 7 and 8 shows a typical case of correlation. As discussed, FIG. 7 is a phase plot of both typical transmit and receive signals. FIG. 8 shows the amplitude plot of a typical received signal. As shown in FIG. 8, there is an initial period of transmission at a preferred frequency identified during a preliminary initial makeup cycle, so as to enable the receive signal to build-up to a constant phase condition, shown in FIG. 7.

The initial build-up record is necessary since in general, the transmission frequency will not be exactly the resonant frequency of the transducer or the pipe wall. The initial build-up period is frequently between 7 and 15 cycles of the transmit frequency. Subsequently, an additional number of cycles at this same frequency and phase is transmitted, so as to establish a constant phase condition, conducive to demodulation by the reference square wave to establish transit time and thus Δt. The number of such cycles is determined by the relation between the transmit frequency and a demodulation clock counter frequency (CLK), chosen so that there are a whole number of cycles of the counter frequency (CLK) in the time during which the demodulation is conducted. This is necessary to insure against a large degree of demodulation data scatter. This will be explained in greater detail below.

Since both upstream and downstream transmissions have the same marker placement and characteristics, it is expected that demodulation of both upstream and downstream receive signals will produce an identical phase detection "shape" at the time of marker arrival. This permits the upstream and downstream marker shapes to be correlated against each other to insure that the phase flow phase detection window is open at the same relationship to the markers for both windows, i.e., the windows are in registration. If this is not found to be true, the flow data obtained during that period of time is rejected, and the windows are repositioned to eliminate this potential error in both flow rate detection and in determination of the liquid's sonic propagation velocity VS, which is simply the sonic path length divided by the measured TL.

TL can be obtained directly from the absolute time of arrival of the upstream and downstream markers. One means is by noting that the beginning of arrival of the marker causes the steady state phase shift which existed during the flow data collection phase detection window to change abruptly, as shown in FIG. 7. It is possible to use a circle function to compute the actual beginning of the marker, by treating it as a tangent to a circle which generates the sinewave like shape of the marker phase pattern itself.

In cases where the Q of the signal is low, the marker phase characteristic is quite linear, so that a linear projection can be used to determine the location of the marker.

Generally, $TL=TN-T_{DEL}$, where $T_{DEL}$ is the sum of the known time delays other than the time that the sonic energy is traversing the fluid. The time TN is the overall transit time between transmission and reception, which is known based on the time between marker transmission and marker receipt.

The use of phase correlation assures that both the upstream and downstream flow phase detection windows are in the same absolute and relative relationship to the phase markers embedded in the upstream and downstream transmit signals. This is essential in avoiding flow error, as may be best understood by examining the way in which flow is actually detected.

With reference to FIG. 7, the receive signal consists essentially of a sinusoidal waveshape, starting at a low amplitude, and building up to a steady state amplitude, which steady state persists for a number of cycles, e.g., at least 20 cycles. This is the result of having transmitted, e.g., at least approximately 30 cycles of a frequency determined by the wall thickness and material of the pipe.

The reason for this number of cycles (i.e., 30 cycles) is that flow metering systems, e.g., Controlotron systems, use phase detection to determine the amount of time shift of the received signal caused by flow, relative to a transmit relative reference, a square wave of the same frequency as transmitted. Phase detection is accomplished by arranging the position of the reference square wave in quadrature to the variable position of the actual liquid receive signal, as controlled by a servo which positions the reference square wave periodically to maintain quadrature within a small difference, typically within one or only a few cycles of a high frequency oscillator from which the reference square wave is itself synthesized. To accomplish this requires that the receive signal be of the same frequency as the reference, or very close to it, intrinsically requiring that during the period of such measurement its frequency is in the steady state region.

Figure 9:
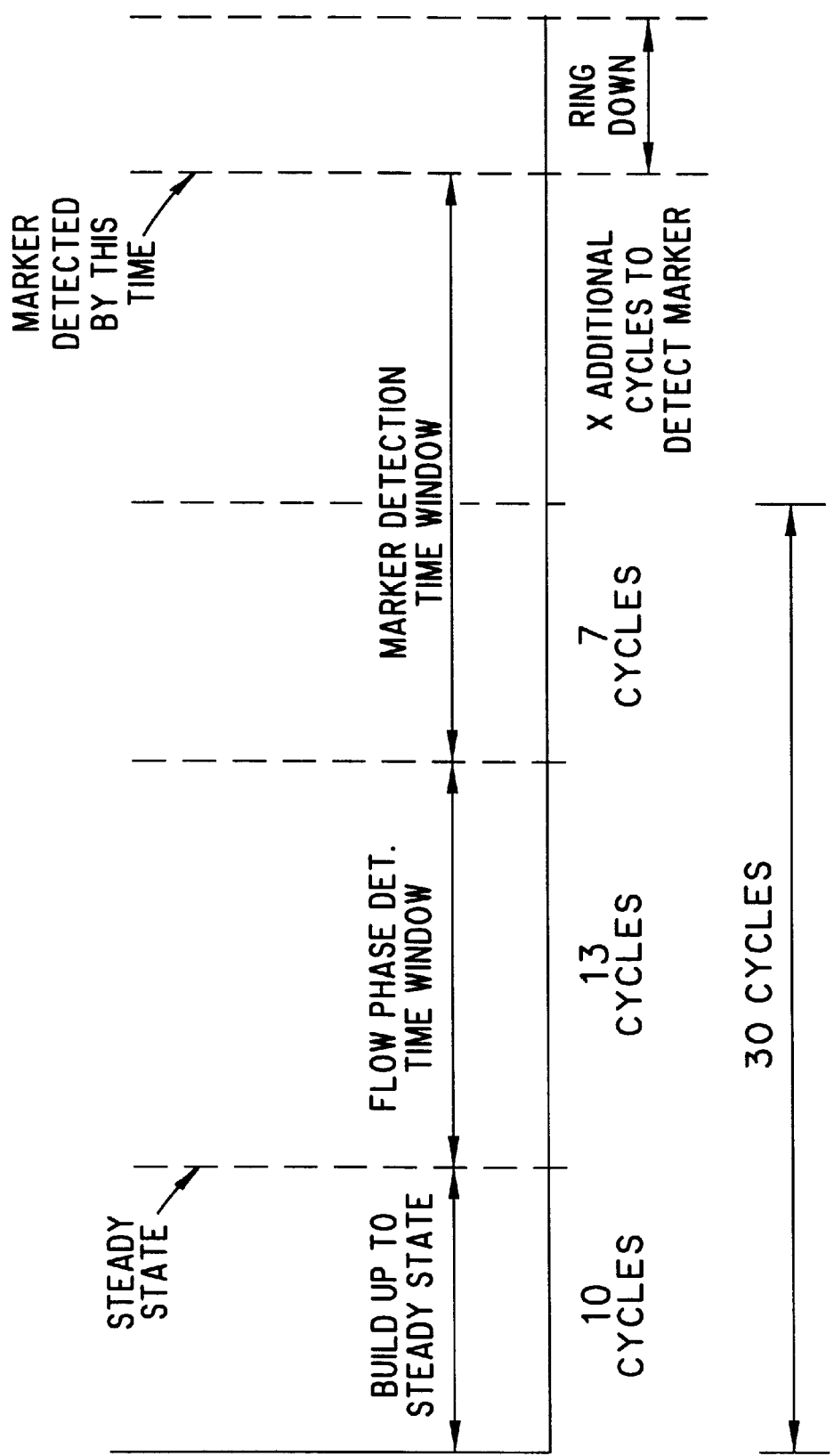
FIG. 9 illustrates the timing windows of the invention including a flow phase detection window and a correlation marker phase detection window.

For reasons of reduced data scatter, it is important that a prescribed number of cycles of receive signal be detected for flow rate determination. For example, in the Controlotron 1010 system, this number is 13 cycles. This is shown in FIG. 9, where the flow phase detection window is indicated as being 13 cycles long. Since it usually takes the transmission of up to 10 cycles for the received signal to reach steady state, at least 23 cycles must be transmitted up to the end of the flow phase detection window. Since a steady state region is also necessary for the marker itself to determine the marker location, 4 to 7 additional cycles are transmitted as an initial part of a following correlation phase detection window, after the 13 cycles used for flow rate detection. This totals up to 30 cycles, as shown in FIG. 9. The marker detection time window contains an additional number of cycles (X), as shown in FIG. 9, for detecting the marker. The marker detection time window is thus illustratively 7+X cycles.

Accordingly, around 30 cycles are transmitted prior to shifting the phase of transmit to establish the first marker. This number may change if it is decided that less than 10 cycles are needed to reach steady state for flow detection, or less than 7 cycles are needed as steady state prior to the marker. In fact, the number of cycles transmitted after the first marker is also variable, and is dependent on the number of cycles needed by the system for the marker to reach its steady state change of phase condition. If more than one marker is transmitted, each starting only after the previous marker's phase change has become clearly established, additional transmit cycles will be needed. Typically, from 7 to 20 cycles are transmitted after the first marker is transmitted.

To determine the upstream and downstream transit times, the following is done. First, the flow phase detection window is initially located so that it begins just after the completion of the initial non-steady state signal build up region. See FIG. 9. This is accomplished by knowing that if the flow phase detection window opens, say, 20 cycles before the first marker location then it will allow the 7 cycles needed for the marker to follow the 13 cycles of steady state receive signal needed for the flow phase detection window. As shown in FIG. 9, the end of the 13 cycle flow phase detection window, which is actually the same as the beginning of the correlation phase detection window, is 7 cycles before the detected first marker.

It is known exactly when the 13 cycle flow phase detection window becomes active, since this window is generated by a precision counter and high frequency precision oscillator. All that is then needed to determine the transit time is to know how far the receive signal in the flow phase detection window is from quadrature with the window itself. This is done by a phase detector. If the receive signal is in quadrature, as determined by a high frequency counter feeding the phase detector, then the receive signal is exactly ¼ of a period of transmit frequency after the beginning of the flow phase detection window time of opening, as previously determined. If it is later or earlier, the condition of the phase detection counter output value, averaged over the 13 cycles of the receive signal it monitors, is converted to equivalent time delay (transit time). The above described flow phase detection is performed independently for both upstream and downstream receive signals. In each case, the flow phase detection window is defined based on the detection of the marker.

The resolution of this determination, averaged over the usual period of flow data output computation is in the range of fractions of a picosecond, accomplishing extraordinary flow detection sensitivity. Both upstream and downstream transit times are computed independent of each other, and the determination of the time difference Δt is done mathematically. Also, the absolute arrival time needed to compute TL is determined by averaging the arrival time of the up and down markers, and determining the elapsed time from the known time at which these markers were transmitted. This computation actually takes into account the position of the up and down windows relative to the receive signal to assure that the computed average TN time is not affected by flow rate.

Figure 4:
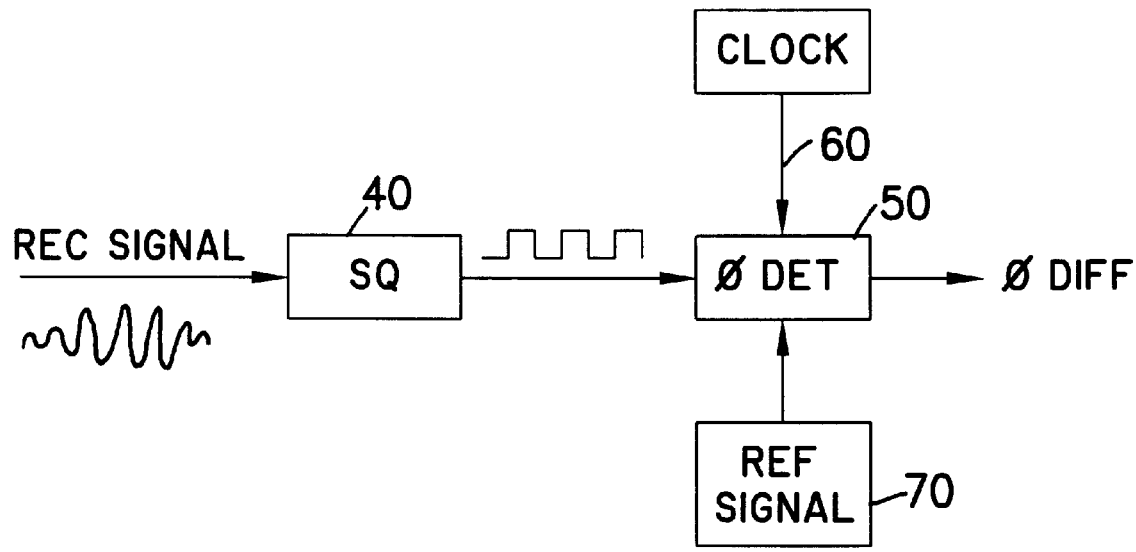
FIG. 4 is a block diagram of an embodiment of a circuit showing the method of phase detection used in the present invention.

FIG. 4 is a block diagram of an embodiment of a phase detection system for detecting the arrival time of the marker and the phase change for determining transit time of the upstream and downstream received signals. Thus, the phase detection system is used both for determining the arrival time of the marker by detecting the sudden change of phase caused by the marker and the time delay (as determined by the change of phase) caused by transmission through the fluid in the pipeline.

The detected receive signal with the embedded marker is fed to a squaring circuit 40, resulting in a square wave signal with the marker embedded within the square wave signal. The square wave signal is fed to a phase detector 50 which determines the phase difference. The phase detector 50 is fed with a high frequency asynchronous clock (CLK) signal 60 and a reference signal 30. The clock signal has a frequency many times higher than the reference or received signal. The reference signal is a synthesized square wave of the same frequency as the transmit signal and is synchronous to the time at which the transmit signal was sent.

Figure 5:
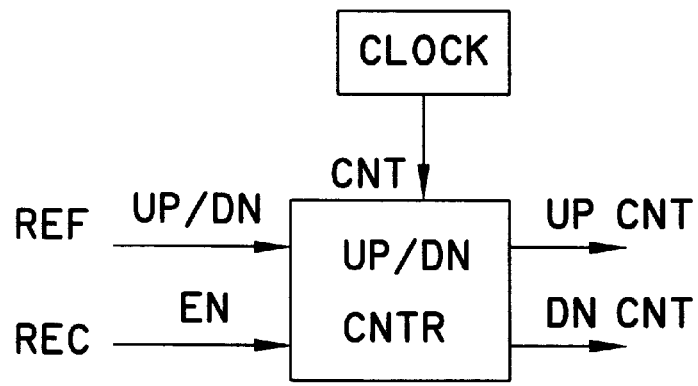
FIG. 5 shows further details of the phase detector according to the present invention.

FIG. 5 shows details of an embodiment of a phase detector. The phase detector may comprise a digital up/down counter which counts the number of pulses of the clock signal during UP and DOWN (DN) periods defined by the reference signal. The receive signal is fed as an enabling input to the up/down counter. When the reference signal is high, the up/down counter will count UP counts if enabled by the receive signal. When the reference signal is low, the up/down counter can count DN counts if enabled by the receive signal. This is illustrated in more detail in FIG. 3 for three examples, showing how the phase can be detected.

Figure 3A:
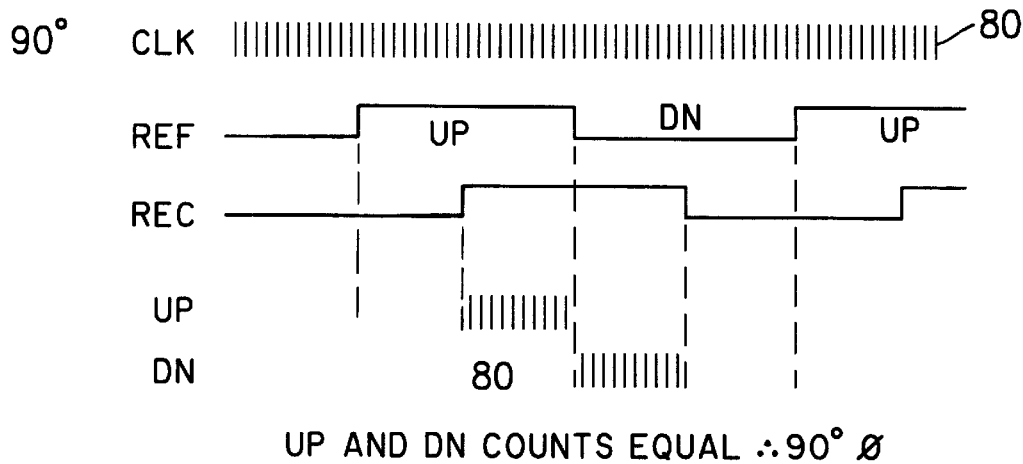
FIG. 3 is a timing diagram showing the method of phase detection.
Figure 3B:
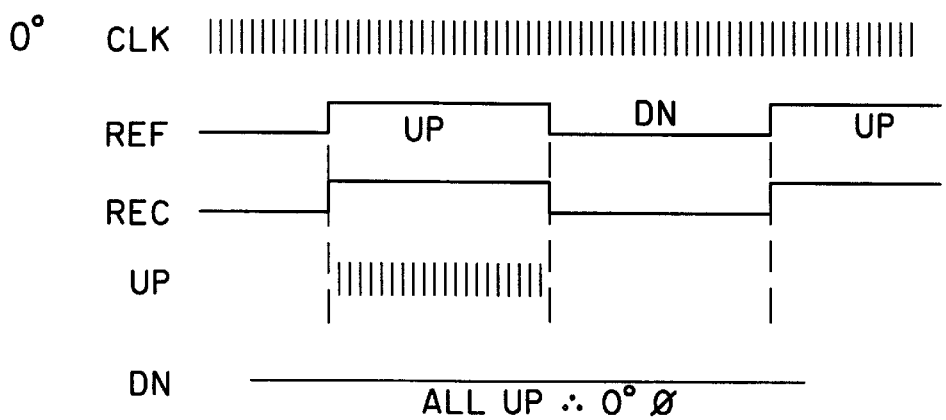
Figure 3C:
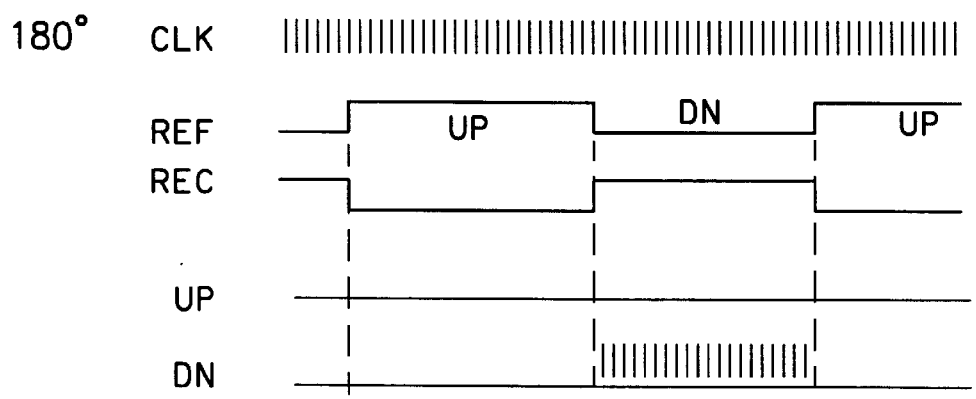

Taking the example of a receive signal which is 90° out of phase with respect to the reference signal, or in quadrature, as shown in part a) of FIG. 3, the reference signal is divided into UP and DN portions, as determined by the level of the reference signal. If the receive signal is 90° out of phase lagging, the up/down counter shown in FIG. 5 will count a number of clock (CLK) pulses 80 during the time when the reference signal is in its UP portion and the receive signal is also high. Similarly, when the reference signal is DN, if the receive signal is high, a number of DN counts will be counted by the up/down counter. Since the receive signal is 90° out of phase with respect to the reference signal, the number of UP and DN counts will be exactly equal, and hence the determination is that the two signals are 90° out of phase. This phase difference corresponds to a precise amount of time delay from transmission through the pipeline to reception (transit time).

In part b) of FIG. 3, an example is shown for the situation where the reference and receive signals are in phase. Because the receive signal is exactly in phase with the reference signal, only UP counts will be counted by the up/down counter i.e., the counter counts UP counts only because the receive signal enables the counter only during UP portions of the reference signal. During DN portions of the reference signal, the receive signal is low, so no DN counts are produced.

In part c) of FIG. 3, an example is shown for when the reference and receive signals are 180° out of phase. As shown there, the receive signal only enables the counter during the time when the reference signal is DN, and consequently, the up/down counter counts only DN counts and the phase difference is 180°.

As is obvious from the above to those of skill in the art, if the reference and receive signals have some other phase difference, the relative number of UP and DN counts will be different and will determine the phase difference. For example, if the receive signal is 45° behind the reference signal, the number of UP counts will be three times the number of DN counts. Put another way, in a full cycle of the receive signal, three quarters of the counts will be UP counts and only one quarter of the counts of the clock frequency will be DN counts.

In this way, the phase difference can be accurately determined, and from the phase difference, the time delay from transmission to reception. This can be done for both upstream and downstream signals, and from the two time delays, the value Δt can be determined.

Furthermore, the sudden phase change caused by the marker is also determined by the phase detector. Based upon the known phase difference caused by the phase marker, the precise location of the phase marker can be determined. For example, if the phase marker embeds a phase change of 60° between the receive signal and the reference signal, i.e. minus 60°, then the relative number of UP counts and DN counts would be such that there are twice as many UP counts as DN counts, i.e. in a full cycle, two thirds of the clock frequency counts will be UP counts.

In this manner, the described invention can determine the phase difference between the receive and reference signals based upon the relative number of UP and DN counts and thus the upstream and downstream transit times and the value of Δt. By positioning the flow phase detection window for upstream and downstream receive signals in precise correlation with each other and the received signal, based on the marker detection, the valve of Δt, as well as TL, will be accurate, leading to accuracy in flow measurement.

Figure 10:
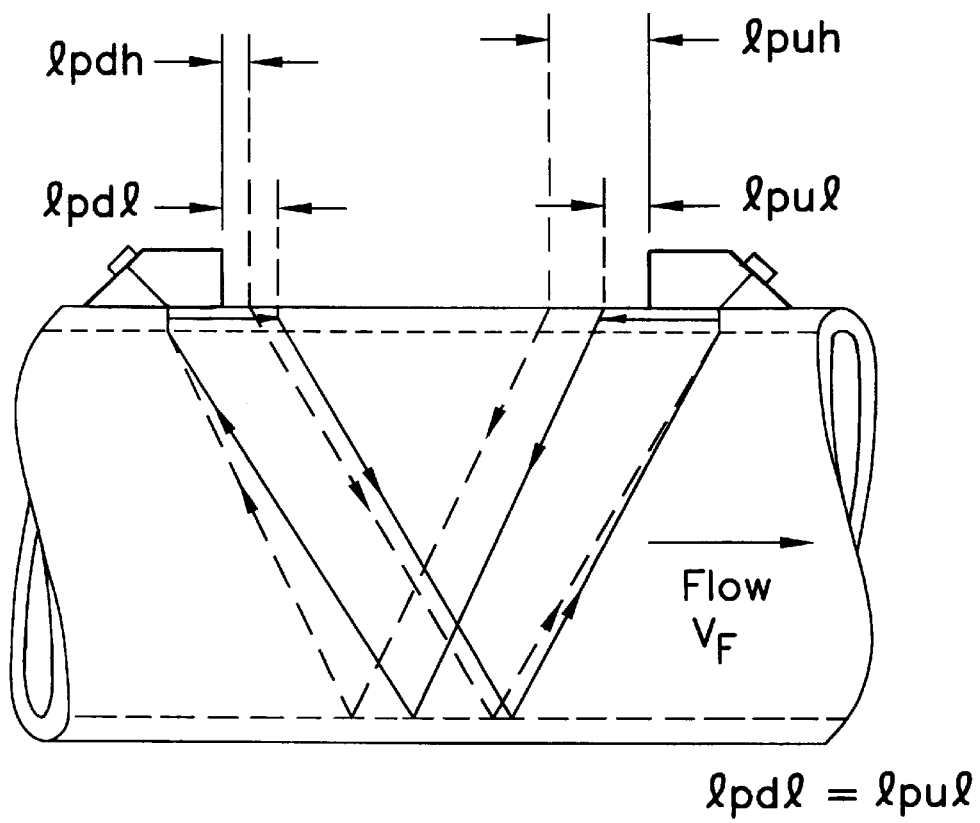
FIG. 10 illustrates the principle of "beam blowing".

In larger pipes, and at higher flow rates, the location on the pipe wall from which the sonic energy emerges to be received at the receive transducer can be significantly different from the location at which the beam emerges at lower flow rates. As shown on FIG. 10, this is due to "beam blowing". As shown, the effect of flow VF is to move the apparent emergence point (as opposed to the actual emergence point) closer to the downstream transmit transducer and further from the upstream transmit transducer. FIG. 10 shows that the low flow rate paths (solid lines) are approximately the same for upstream and downstream signals. Thus, $lp_{ul}=lp_{dl}$. At higher flow rates, the paths, shown by dashed lines, are different. In particular, $lp_{Uh}>>lp_{Dh}$. Thus, there results a different distance of pipe travel before the beam enters the liquid between the up and downstream transmission directions. For smaller pipes, and/or low flow rates, the effect is less noticeable.

Applicant has previously discovered the existence of a sonic waveguide property in all pipes, in which a sonic wave will propagate with essentially equal phase and group velocities if the injected signal is at the resonant frequency of the pipe wall, and the phase velocity of the injected sonic signal matches the transverse mode sonic velocity as it travels axially down the pipe wall. See U.S. Pat. Nos. 3,987,674 and 4,475,054. The resonant frequency is determined by the wall thickness and the longitudinal wave velocity of the pipe material. The phase velocity is determined by the pipe material, and to some extent is affected by the wall thickness, since the actual velocity is somewhat different from that of the bulk material.

If the transducer's sonic signal has a transmit frequency which matches a pipe's resonant frequency, and its injection angle matches the phase velocity of the transducer housing to the transverse mode phase velocity in the pipe wall material, then the shape and phase characteristics of the sonic wave in the pipe wall remain essentially constant as the wave travels axially down the pipe wall. Thus, even though, due to beam blowing, the amount of pipe travel may be different in the upstream and downstream directions, the resultant signal shape and phase characteristics will be essentially identical. Therefore, even though the sonic beam may be blown by high flow rates, the marker phase characteristics will remain identical, or at least sufficiently so for successful flow phase detection window position correlation.

Since a transducer as described above is the only type of transducer that can avoid beam blowing effects, it necessarily follows that only the so-called Controlotron wide beam transducer (U.S. Pat. No. 3,987,674), which matches the frequency and phase velocity waveguide characteristics of a particular pipe, can permit successful window position correlation independent of the effects of high flow velocity beam blowing. Therefore, all transducers which operate at a fixed single frequency, or a group of frequencies, none of which match the pipe's resonant frequency, and whose phase characteristic is not specifically matched to the material of a given pipe, cannot avoid a change in its amplitude shape and phase characteristic due to beam blowing, with consequent deterioration of both phase and amplitude correlation methods.

In order to provide the match to the pipe phase characteristic, the wide beam transducer is manufactured so that the longitudinal wave angle from the normal in the transducer is such as to produce a transverse sonic beam direction in the pipe wall which is axial, in the direction of the pipe axis, or 90 degrees from normal. This transducer angle is determined by Snell's law, and is therefore dependent on the sonic propagation of the transducer material as well as the sonic velocity of the sonic beam in the pipe material. Since it is desirable to excite the transverse wave mode of the pipe, it is this velocity which is used to compute the transducer beam angle. For steel pipe, and with a transducer material whose sonic velocity is around 97000 inches per second, the transducer angle will approximate 57 degrees from the normal.

Figure 2A:
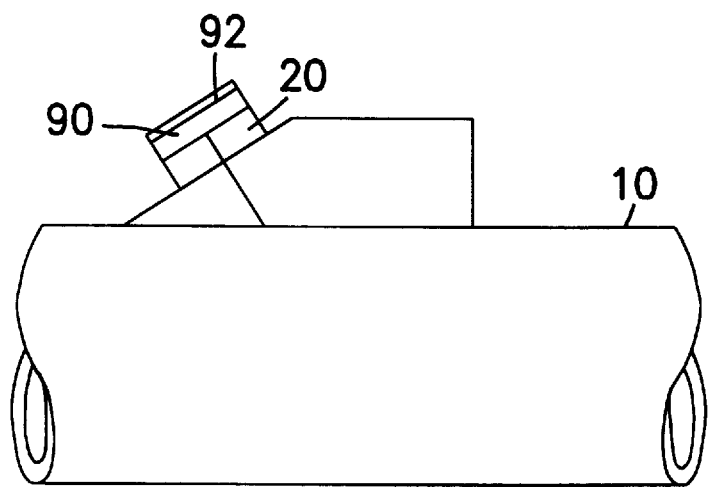
FIGS. 2 and 2B show how an ultrasonic transducer may be damped to reduce its transmission of delayed, stored sonic energy due to internal reflections of longitudinal and mode converted shear sonic waves.

In order to match the resonant frequency of the pipe wall, it is necessary to account for the wall thickness tolerances of the pipe, as well as to be prepared to generate the different frequencies for the different pipe wall thickness for the many "schedules" of pipe which may be encountered. In order to minimize the number of different transducers which may be required, it is essential to produce a transducer which is capable of operating over this wide range of frequencies. Since piezoelectric materials normally used are generally highly resonant, (high Q), it is desirable to reduce this Q. This can be done by suitably damping the piezoelectric crystal, or preferably, by placing an anti-resonant structure in contact with the crystal itself. This may be done as shown in FIG. 2A, in which an anti-resonant plastic disc 90 is placed on the side of the crystal 20 not in contact with the transducer beam injection surface. To condition the degree of anti-resonance, a damping compound 92 may be placed on the opposite side of the plastic disc from its contact surface with the crystal. In any event, it is essential to provide a transducer capable of operating at a wide range of frequencies. A range of +/−20% around a center frequency is considered practical.

In addition to damping the piezoelectric crystal to help generate a low Q signal for most accurate phase marker detection, it is desirable to prevent the internal transducer reflection of the sonic signal. The transducer injects sonic flow detection signal into the pipe at the contact point with the pipe (the transducer footprint) and it is desirable to prevent the signal from again reaching this surface. If permitted, it is obvious that these internally reflected signals would corrupt the phase correlation region, affecting accurate detection of the phase marker.

Figure 2B:
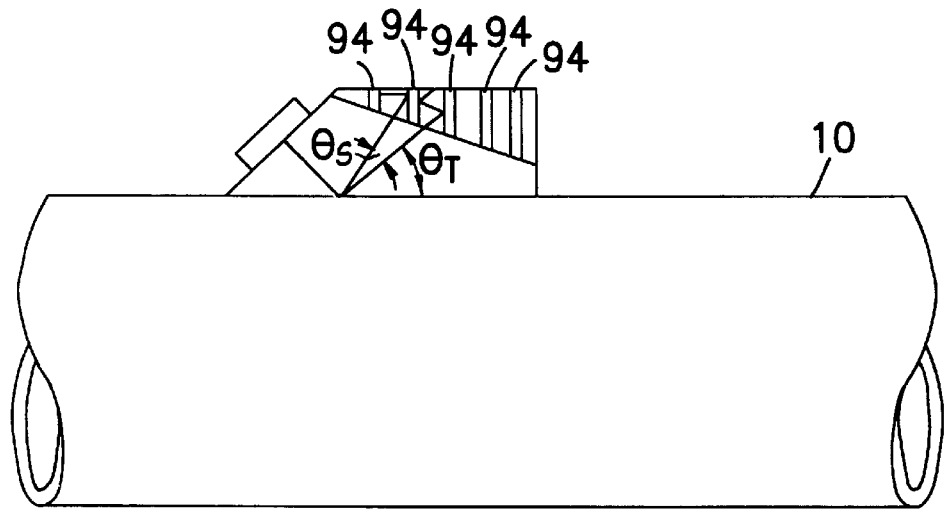

To accomplish this, as shown in FIG. 2B, a sonic labyrinth is preferably provided by making appropriate slots 94 which "catch" both the reflected longitudinal and mode converted shear wave beams and subject them to many internal reflections. Each impingement against the slot wall, within which a viscous material, such as tar, glue or a suitable viscous plastic material has been placed, subjects the entering reflections to successive attenuation and as well on the way out of the labyrinth. This effectively reduces the effect of the residual reflected sonic waves by as much as 10:1, greatly reducing the effect on the correlation shape.

In addition, the aforementioned internal echo damping serves to reduce transient after-ringing. Such ringing serves to make the effective transient period large, thus enlarging the actual active transient period. This results in a longer period of pipe noise, which especially affects reflection mode transducer mounting by permitting noise free acceptance of liquid signal generated for applications involving low sonic velocity liquid which call for close spacing of the transducers. When the after ringing is eliminated, the transverse based pipe noise is reduced considerably so that its resultant effect of causing drift of the detected flow rate is eliminated.

In order to drive the transducer at the frequency demanded by the pipe wall, it is essential that the flow computer, which generates the transducer transmit signal, test the pipe at the time of initial transducer installation to determine the pipe's resonance frequency. This is done by a process called initial makeup, in which a variety of frequencies are generated and the optimum frequency is selected by examination of the resultant amplitude and/or phase characteristics.

It should be noted that the amount of pipe wall that the beam travels also changes due to changes in the refraction angle of the beam due to changes in sonic propagation velocity of the liquid. However, in this case, the change in pipe travel in the upstream and downstream directions is equal, making any change in phase of the signals equal, and preserving the ability to correlate the phase signatures, even if different from that offered at other liquid sonic propagation velocities. However, since a change in phase characteristic would potentially cause a change in determination of the absolute arrival time of the upstream and downstream signals, from that determined at different liquid sonic propagation velocities, a non-widebeam transducer would likely produce error in computation of TL, which as noted above, would result in a flow rate computation error. The wide beam transducer will avoid such error since its sonic signal will be essentially independent of flow rate, and be of low Q characteristic.

The described phase correlation technique is a powerful method of assuring that the ultrasonic detection of both transit-time and transit-time difference between upstream and downstream sonic transmissions is free of both misregistration and misacquisition error in determining absolute arrival time. Use of a positive emplacement of a phase marker, rather than use of naturally occurring phase changes, assures accurate sonic propagation velocity determination for accurate flow measurements. Performing this correlation on a real time basis, coincident with the measurement of flow itself, assures against undetected shifts of flow phase detection window position, and consequent error in flow measurement.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Apparatus for determining the arrival time of a sonic signal transmitted through a fluid medium flowing in a vessel comprising:

a transmitter for generating a sonic signal for transmission through the fluid in the fluid carrying vessel, the sonic signal having at least one marker embedded therein;

a receiver for receiving the marked sonic signal after transmission of the signal in the fluid;

a detector for sensing the marker in the marked sonic signal at the receiver; and the transmitter and receiver each comprising a wide beam ultrasonic transducer.

2. The apparatus of claim 1, further comprising a circuit for determining e time of arrival of the marker.

3. The apparatus of claim 2, further comprising a circuit using the time of arrival of the marker to determine the transit time of the sonic signal through the fluid.

4. The apparatus of claim 3, further comprising a transmitter transmitting a marked sonic signal in both an upstream direction and a downstream direction and a circuit determining a difference in transit times in the upstream and downstream directions.

5. The apparatus of claim 4, further comprising means determining an average transit time from the transit times in the upstream and downstream directions.

6. The apparatus of claim 5, further comprising means using the difference in transit times and the average transit time to determine flow rate of fluid in the vessel.

7. The apparatus of claim 1, further comprising a generator providing a flow detection time window at a predefined time after the beginning of transmission of said sonic signal and a circuit for determining the amount of time delay in the sonic signal at the receiver due to the transmission through the fluid in the vessel to the receiver during said time window.

8. The apparatus of claim 7, further comprising a generator providing a marker detection time window at a predetermined time after the beginning of transmission of said sonic signal and a circuit for detecting the marker in the received signal during the marker detection time window.

9. The apparatus of claim 8, further comprising a circuit determining the time of arrival of the marker in the received signal in the marker detection time window.

10. The apparatus of claim 8, wherein the predetermined time comprises a preset number of cycles of the sonic signal.

11. The method of claim 8, wherein the marker detection time window comprises a preset number of cycles of the sonic signal.

12. The apparatus of claim 7, wherein the predefined time comprises a preset number of cycles of the sonic signals.

13. The apparatus of claim 12, wherein the preset number of cycles to the predetermined time at which the marker detection time window opens is greater than the number of cycles to the predefined time at which the flow detection time window opens.

14. The apparatus of claim 9, further comprising means using the arrival time of the marker in the marker detection time window to adjust an opening time of the flow detection time window for determining the amount of time delay in the sonic signal at the receiver.

15. The apparatus of claim 14, further comprising a circuit for determining the time of arrival of the marker for both the sonic signal transmitted in the upstream direction and the sonic signal transmitted in the downstream direction and means adjusting the position of the flow detection time window for both the signal transmitted in the upstream direction and the signal transmitted in the downstream direction so that the respective flow detection time windows are positioned in the same relationship to the marker.

16. The apparatus of claim 14, further comprising a generator opening said flow detection time window initially at a predetermined time after transmission when the sonic signal is expected to be received at the receiver.

17. The apparatus of claim 4, further comprising a circuit determining said upstream and downstream transit times a plurality of times.

18. The apparatus of claim 2, wherein the marker comprises a change of phase marker in the sonic signal.

19. The apparatus of claim 15, wherein the marker comprises a change of phase marker and the circuit for determining the amount of time delay in the flow detection time window comprises a circuit determining a phase difference of the received signal with respect to a reference signal and for detecting the marker by detecting the change of phase caused by the marker.

20. The apparatus of claim 18, wherein the circuit for determining the time of arrival of the marker comprises a circuit detecting the change of phase of the received signal corresponding to the change of phase marker.

21. The apparatus of claim 14, wherein the circuit for determining the amount of time delay in the flow detection time window comprises a phase detector detecting the change of phase of the received signal and wherein the time delay corresponds to the change of phase with of the received signal with respect to a reference signal.

22. The apparatus of claim 21, wherein the circuit detecting the change of phase of the received signal comprises:

a phase detection circuit having a clock frequency signal, the received signal and a reference signal of the same frequency as the received signal and synchronized to the transmitted signal as inputs;

the phase detection circuit comprising a counter for counting clock frequency signals;

the counter being enabled to count said clock frequency signals by said received signal;

the counter counting the number of clock frequency signals during respective half cycles of the reference signal when enabled by said received signal;

thereby resulting in respective clock frequency signal counts during respective half cycles of the reference frequency signal;

the relative number of said counts of clock frequency signals in said respective half cycles of the reference signal determining the phase difference between said received signal and the reference signal; and a circuit using the detected phase difference to calculate the time delay due to transmission from the transmitter to the receiver.

23. The apparatus of claim 22, further comprising a squaring circuit for squaring up said received signal prior to providing the received signal to the phase detection circuit.

24. The apparatus of claim 1, further wherein the transducers are matched to the frequency and phase velocity waveguide characteristic of the fluid carrying vessel.

25. The apparatus of claim 24, further comprising a damping component on the transducer to reduce the Q of the transducers.

26. The apparatus of claim 25, further comprising a damping component on the transducers comprising an anti-resonant component on a side of the transducer not in contact with a beam injection surface of the transducer.

27. The apparatus of claim 26, further comprising a damping component on the anti-resonant component on a side thereof opposite the side contacting the transducer.

28. The apparatus of claim 25, wherein the damping component comprises a plurality of slots in a housing of the transducer, the slots being filled with a damping compound to reflect and absorb internal reflections of ultrasonic signals generated by the transducer.

* * * * *